Nov. 21, 1961 G. VERBEEK Plant Pat. 2,105
ROSE PLANT
Filed Dec. 16, 1960
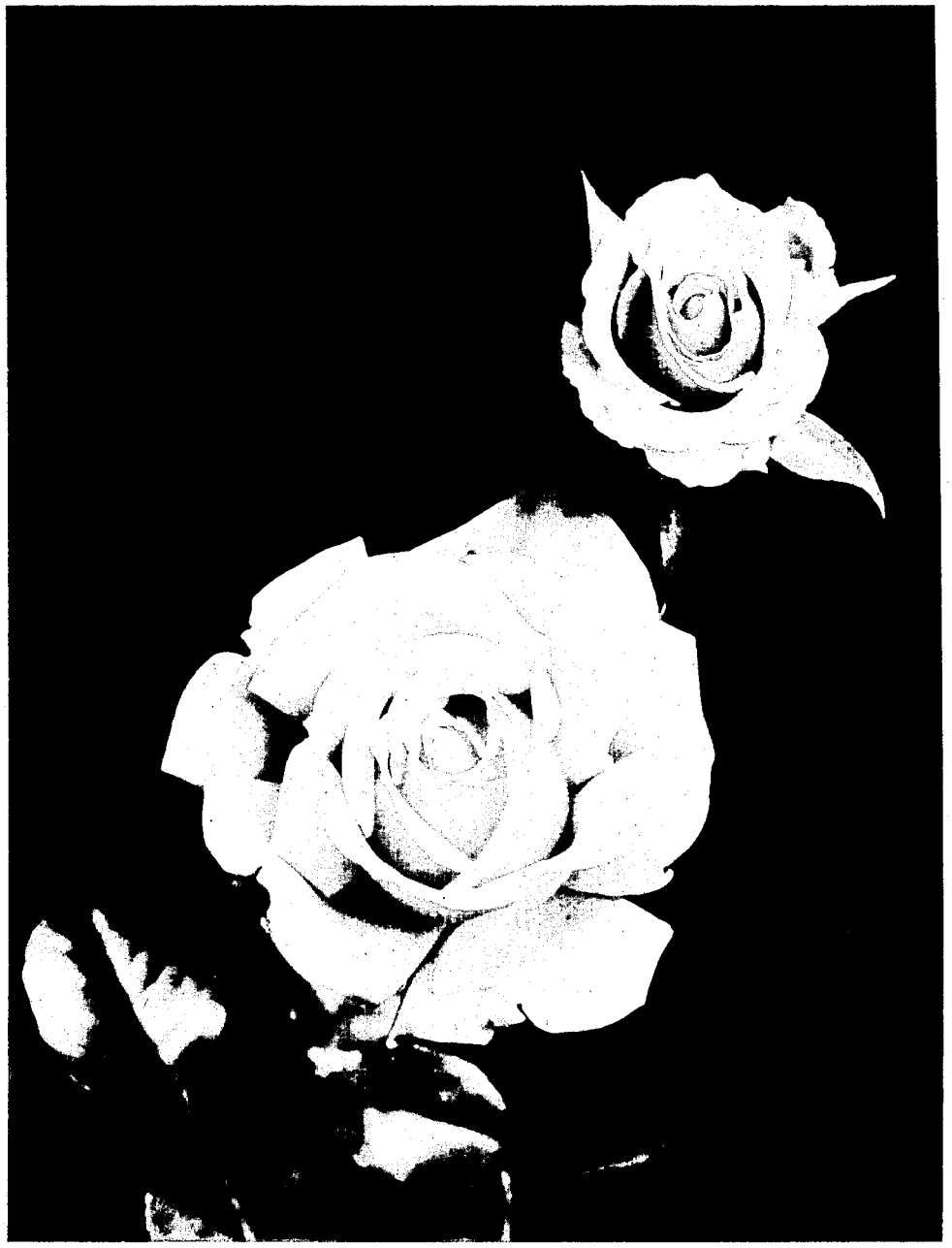
INVENTOR
Gysbert Verbeek
BY Robb & Robb
ATTORNEYS United States Patent Office Plant Pat. 2,105
Patented Nov. 21, 1961

2,105
ROSE PLANT

Gysbert Verbeek, Aalsmeer, Netherlands, assignor to Carlton Rose Nurseries, Carlton, Oreg., a corporation of Oregon Filed Dec. 16, 1960, Ser. No. 76,427
Claims priority, application France Apr. 11, 1960
1 Claim. (Cl. 47—61)

The present invention relates to a new and distinct variety of rose plant of the hybrid tea class, which was originated by me by crossing the variety "Tawny Gold" (U.S. Plant Patent No. 950) with an unnamed and unpatented seedling of "Baccara" (U.S. Plant Patent No. 1,367) × an unnamed and unpatented seedling of unidentified origin.

As the result of this breeding, I have produced a new rose variety which is endowed with the following combination of outstanding characteristics which distinguish the same from its parents, as well as from all other varieties of which I am aware:

(1) Very glossy green foliage;

(2) Relatively large blooms which are larger than those of the parent variety "Tawny Gold";

(3) Long flower stems which are longer than those of "Tawny Gold";

(4) A distinctive and attractive yellow general color tonality of the flowers ranging from Buttercup Yellow in the newly opened flowers to Golden Yellow in the 3-day open stage, these colors being more striking and attractive than the flower color of "Tawny Gold"; and (5) Strong tea fragrance of the flowers.

Asexual reproduction of my new variety by grafting, as performed by me at Aalsmeer, Holland, shows that the foregoing characteristics and distinctions come true to form and are established and transmitted through succeeding propagations.

The accompanying drawing shows typical specimens of the flowers and foliage of my new variety in different stages of development, and as depicted in color as nearly true as it is reasonably possible to make the same in a color illustration of this character.

The following is a detailed description of the new variety, with color terminology in accordance with the Horticultural Colour Chart issued by the British Colour Council in collaboration with The Royal Horticultural Society, except where general color terms of ordinary dictionary significance are obvious:

Type: Half-hardy; greenhouse and outdoor; seedling; for cut flowers and for garden decoration.

Class: Hybrid tea.

Breeding: Seedling.

*Seed parent.*—"Tawny Gold."

*Pollen parent.*—An unnamed seedling of "Baccara" × an unnamed seedling of unidentified origin.

Propagation: Holds its distinguishing characteristics through succeeding propagations by grafting.

*Flower*

Locality where grown and observed: Aalsmeer, Holland.

Continuity: Continuous.

Fragrance: Penetrating. Nature—tea.

Flowers borne: Several to stem; in regular flat clusters; on strong stems of medium-long length.

Quantity of bloom: Free, both outdoors and in greenhouse.

Bud:

*Peduncle.*—Medium length; medium caliper; erect; medium smoothness; with numerous red thorns. Color—bronze.

*Before calyx breaks.*—Size—large. Form—oval; with a conspicuous neck; sometimes with foliaceous parts extending beyond the tip of the bud equal to ½ or more of its length. Color—Indian Yellow, Plate 6.

*As calyx breaks.*—Color—Indian Yellow, Plate 6.

*As first petal opens.*—Size—medium. Form—ovoid. Color: outside—Chromium Yellow, Plate 605; inside—Chromium Yellow, Plate 605/1.

*Opening.*—Opens up well.

Bloom:

*Size (when fully open).*—Large. Average size when fully expanded—from 4½ inches to 5½ inches.

*Petalage.*—Semi-double; from 22 to 30 petals; arranged regularly.

*Form.*—Full at first, but becoming flat; petals at first being rolled outward, but later becoming more loosely rolled outward at maturity.

Petals:

*Texture.*—Thin.

*Appearance.*—Inside—satiny. Outside—satiny.

*Shape.*—Outside—ovate. Intermediate—ovate. Inside—round.

This description of a newly opened flower was made from a rose grown in a greenhouse in the month of August at Aalsmeer, Holland:

*Color.*—Outer petal: outside surface—Chromium Yellow, Plate 605; inside surface—Chromium Yellow, Plate 605/1. Intermediate petal: outside surface—Chromium Yellow, Plate 605; inside surface—Chromium Yellow, Plate 605/1. Inner petal: outside surface—Buttercup Yellow, Plate 5; inside surface—Buttercup Yellow, Plate 5/1.

This description was made from a rose that was open for 3 days in a greenhouse in the month of August at Aalsmeer, Holland:

*Color.*—Outer petal: outside surface—Chromium Yellow, Plate 605; inside surface—Chromium Yellow, Plate 605/1. Inner petal: outside surface—Chromium Yellow, Plate 605/1; inside surface—Chromium Yellow, Plate 605/1.

*General color effect.*—Newly opened flower—Buttercup Yellow. 3-days open—Golden Yellow.

*Behavior.*—Drop off cleanly; fading yellow.

*Flower longevity.*—On bush in garden—5 days during August and September. Cut roses grown outdoors and kept at living-room temperatures—4 days during August and September. Cut roses grown in greenhouse and kept at living-room temperatures—4 days during August and September.

*Reproductive organs*

Stamens: Many (from 170 to 190); arranged regularly about pistils. Color—Majolica Yellow, Plate 09/1.

Filaments: Medium length; without anthers. Color—yellow.

Anthers: Medium large; all open at once. Color—yellow.

Pollen: Very abundant. Color—gold.

Pistils: Many.

Styles: Even length; short; thin; bunched.

Stigma: Color—Cadmium Orange, Plate 8/2.

Ovaries: All enclosed in calyx.

Hips: Short; flat; smooth; thick walls. Color—green, but turning yellow at maturity.

Sepals: Falling moderately soon; from moderate to medium length; recurved. Color—green, changing to brown at maturity.

Seeds: Very many; large.

*Plant*

Foliage:

*Leaves.*—Compound of 5–7 leaflets; normal abundance; moderately large; heavy; glossy.

*Leaflets.*—Shape—oval. Base—round. Margin—simply serrate.

*Color.*—Mature: upper surface—glossy dark green; under surface—lighter green. Young: upper surface—dark bronze; under surface—bronze.

*Rachis (the supporting stem of the compound leaf).*—Medium. Upper side—hairy. Under side—moderately prickly.

*Stipules.*—Medium length; narrow; with short points turning out at an angle of less than 45°; recurved toward the stem.

*Disease resistance.*—Very good resistance to mildew and blackspot as determined by comparison with other varieties grown under the same cultural conditions at Aalsmeer, Holland.

Growth:

*Habit.*—Bushy.

*Growth.*—Free.

*Canes.*—Heavy.

*Main stems.*—Color — green. Thorns — several; medium length; hooked; with round base; color— reddish. Prickles—few; color—bronze. Hairs—none.

*Branches.*—Color—bronze green. Thorns—several; medium length; hooked downward; with round base. Prickles—none. Hairs—none.

*New shoots.*—Color — bronze. Thorns — several; medium length; hooked downward; with round base. Prickles—few; color—brown. Hairs—none.

I claim:

A new and distinct variety of rose plant of the hybrid tea class, substantially as herein shown and described, characterized particularly as to novelty by the unique combination of very glossy green foliage, relatively large blooms, relatively long flower stems, a distinctive yellow general color tonality of the flowers ranging from Buttercup Yellow to Golden Yellow, and a strong tea fragrance of the flowers.

No references cited.